United States Patent [19]
Burleigh et al.

[11] Patent Number: 4,769,361
[45] Date of Patent: Sep. 6, 1988

[54] METHOD FOR PURIFYING AND ISOLATING TWO IONIC FORMS OF SOMATOMEDIN C

[75] Inventors: Bruce D. Burleigh, Mundelein, Ill.; Darla S. Murphy, Terre Haute, Ind.

[73] Assignee: International Minerals & Chemical Corp., Terre Haute, Ind.

[21] Appl. No.: 894,216

[22] Filed: Aug. 7, 1986

[51] Int. Cl.$^4$ .................. A61K 37/24; C07K 7/10
[52] U.S. Cl. ................................. 514/12; 530/324
[58] Field of Search ...................... 514/12; 530/324

[56]  References Cited
PUBLICATIONS

Chem. Abstr. vol. 103 (1985) 17155.
Chem. Abstr. vol. 103 (1985) 16937.
Chem. Abstr. vol. 104 (1986) 200340.
Chem. Abstr. vol. 105 (1986) 36340.
Chem. Abstr. vol. 107 (1987) 1600.
Chem. Abstr. vol. 107 (1987) 929.
Chem. Abstr. vol. 91 (1979) 188284.
Chem. Abstr. vol. 92 (1980) 106023.
Chem. Abstr. vol. 96 (1982) 155700.
Chem. Abstr. vol. 92 (1980) 140817.
Chem. Abstr. vol. 102 (1985) 106458.
Chem. Abstr. vol. 103 (1985) 116430.

*Primary Examiner*—Delbert R. Phillips
*Attorney, Agent, or Firm*—Thomas L. Farquer; Wendell R. Guffey

[57]  ABSTRACT

Two different ionic forms of somatomedin C (pI 6.4–7.0 and pI 8.3–8.6) are separated and isolated by applying an aqueous solution of somatomedin C to a strong cation-exchange column, eluting the somatomedin C from the column by applying a salt concentration gradient at constant pH and recovering the two ionic forms in different eluant fractions.

13 Claims, 2 Drawing Sheets

```
CC ATG GGT CCA GAG ACG TTG TGT GGC GCT GAG CTG GTG GAC GCT CTG
   Met Gly Pro Glu Thr Leu Cys Gly Ala Glu Leu Val Asp Ala Leu

CAG TTC GTG TGC GGT GAC CGT GGA TTC TAC TTC AAC AAA CCG ACT
Gln Phe Val Cys Gly Asp Arg Gly Phe Tyr Phe Asn Lys Pro Thr

GGT TAC GGA TCC TCC TCG AGG CGT GCT CCT CAG ACT GGA ATC GTC
Gly Tyr Gly Ser Ser Ser Arg Arg Ala Pro Gln Thr Gly Ile Val

GAC GAA TGT TGT TTC CGT TCT TGC GAC CTG AGG CGT CTA GAA ATG
Asp Glu Cys Cys Phe Arg Ser Cys Asp Leu Arg Arg Leu Glu Met

TAC TGC GCG CCG CTG AAA CCG GCG AAG AGT GCA TAA GCT T
Tyr Cys Ala Pro Leu Lys Pro Ala Lys Ser Ala
```

FIG. 1

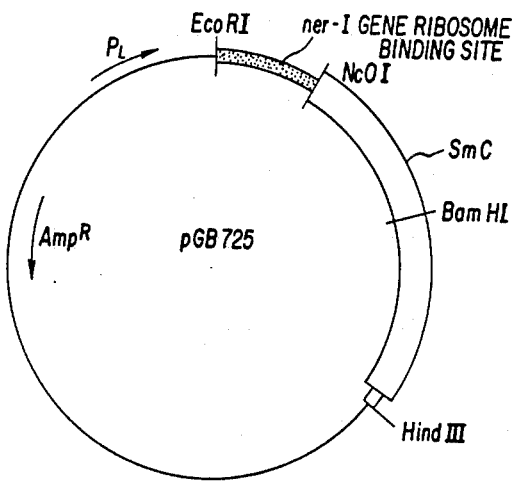

FIG. 2

METHOD FOR PURIFYING AND ISOLATING TWO IONIC FORMS OF SOMATOMEDIN C

BACKGROUND OF THE INVENTION

This invention relates to methods of purifying and isolating two different ionic forms of the polypeptide hormone somatomedin C and to preparations containing each of the pure ionic forms.

The somatomedins are a family of polypeptide hormones which mediate the activity of growth hormones and which also display insulin-like biological activities. The first polypeptides in this family to be purified to homogeneity from plasma were designated insulin-like growth factors 1 and 2 (IGF-1 and IGF-2). The complete amino acid sequence of IGF-1 isolated from plasma was reported by Rinderknecht and Humbel and shown to be homologous to proinsulin (*J. Biol. Chem.*, 253:2769 [1980]). Somatomedin C (SmC) isolated from plasma was shown to be identical in amino acid sequence to IGF-1 (Klapper et al., *Endocrinology*, 112:6, 2215 [1983]). SmC/IGF-1 is a polypeptide 70 amino acid residues in length having disulfide bridges at positions 6-48, 18-61 and 47-52. The predicted pI of SmC/IGF-1, based on its amino acid sequence, is about 8.6.

Svoboda and coworkers reported a procedure for purifying SmC from Cohn fraction IV of human plasma (*Biochemistry*, 19:790-797 [1980]). The procedure involved acid-extracting; cation-exchange chromatography on SP-Sephadex C-25 with elution at 0.2M NaCl, 0.4M NaCl and finally a pH step gradient of pH values of 5.0, 6.0 and 9.0; size exclusion chromatography on a Sephadex G-50 column; flatbed isofocusing; and reverse-phase liquid chromatography. The SmC prepared in this manner was said to have a pI of 8.1-8.5.

Cornell and Boughdady reported the results of various procedures for purifying IGF-1 and IGF-2 from plasma (*Prep. Biochem.*, 12(1) :57 [1982]; *Prep. Biochem.*, 14(2):123 [1984]). Several of these procedures employed a cation-exchange chromatography step on SP-Sephadex C-25. Elution from the column was by stepwise gradient using 0.05M ammonium acetate buffer of pH 6.8 followed by 0.06M ammonium acetate containing 0.12M NH$_3$ (pH 9.6). The active material was said to be eluted in the pH 9.6 fractions.

None of the foregoing papers reporting purification procedures employing an SP-Sephadex C-25 chromatography step indicated that different ionic forms of SmC/IGF-1 were obtained.

Enberg and coworkers reported the purification of SmA by a procedure which involved affinity chromatography on CM-Affigel blue; size exclusion chromatography on Sephadex G-50; cation-exchange chromatography on SP-Sephadex C-25; and reverse-phase liquid chromatography (*Eur. J. Biochem.*, 143:117 [1984]). In the cation-exchange chromatography step, elution from the column was performed using a combined pH/salt gradient of sodium acetate in three steps with pH/molarities of 4.9/0.14, 5.3/0.17 and 7.8/0.20. SmA obtained by this procedure was said to be identical to IGF-1 with the possible exception of a deamidated glutamine residue at position 40.

Recently, two groups have reported the synthesis of SmC in microbial transformants carrying synthetic genes coding for human SmC (Buell et al., *Nuc. Acids Res.*, 13(6):1923 [1985]; European Patent Publication No. 0 123 228). Neither publication reports the isolation of different ionic forms of SmC.

SUMMARY OF THE INVENTION

This invention provides a method of separating and isolating two ionic forms of somatomedin C. In accordance with the teachings of the invention, an aqueous solution of purified or partially purified somatomedin C is applied to a strong cation-exchange column at a pH at which the SmC is stable. The SmC is then eluted from the column at a constant pH by applying an aqueous salt gradient to the column. The two ionic forms (pI's 8.3-8.6 and 6.7-7.0) are then recovered in different eluant fractions.

There is also provided by the present invention a growth-promoting composition comprising somatomedin C having a pI of about 8.3-8.6, being essentially free of deamidated residues at amino acid position 26, and a pharmaceutically acceptable carrier vehicle.

In another embodiment of the invention, there is provided a growth-promoting composition comprising somatomedin C, having a pI of about 6.7-7.0 and having an aspartic acid residue at position 26, being essentially free of somatomedin C having an asparagine residue at position 26, and a pharmaceutically acceptable carrier material.

BRIEF DESCRIPTION OF THE DRAWINGS

FIG. 1 represents the DNA sequence of the synthetic SmC gene insert in pGB725 and its encoded amino acid sequence.

FIG. 2 is a partial restriction map of pGB725.

DETAILED DESCRIPTION OF THE INVENTION

Figure 3:
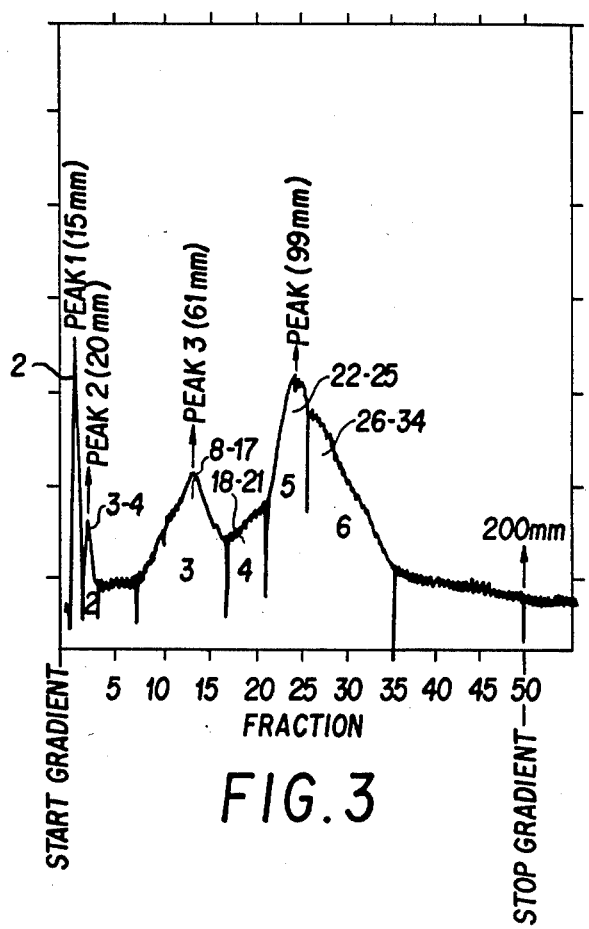
FIG. 3 is a chromatograph obtained by chromatography of SmC on SP-Sephadex C-25.

The invention is based on the discovery that somatomedin C can be isolated in two distinct ionic forms, one having a pI of about 8.3 to 8.6 and the other having a pI of about 6.7 to 7.0. The two ionic forms can be isolated from SmC obtained from natural sources, i.e., from plasma, or they can be isolated from SmC which is synthesized in microbial transformants carrying an expressible recombinant gene coding for SmC. Prior to being subjected to the isolation process of the invention, the SmC is at least partially purified from its source material, preferably to near homogeneity. As used herein, the term "SmC" is considered to be identical in meaning to IGF-1.

SmC which is useful as a starting material in the method of the invention can be purified from Cohn fraction IV of human plasma using known protein purification procedures. (See, e.g., Svoboda et al., *Biochemistry*, 19:790 [1980]; Cornell, H. J. and Boughdady, N. M., *Prep. Biochem.*, 14(2):123 [1984]).

The method of the invention can also be practiced in conjunction with SmC that is synthesized in a microbial host which has been transformed with an expression vector carrying an expressible gene coding for SmC. The work described below was carried out with human SmC (rhSmC) that was synthesized in *E. coli* HB101 cells transformed with pGB725, a plasmid vector carrying a synthetic gene (210-b.p.) coding for the exact 70-amino acid sequence of somatomedin C and an ATG start codon at the 5' end coding for an additional methionine residue. The synthetic gene contains a modified 5'-end in which codons other than the codons of the native DNA sequence were selected for efficient expression in *E. coli*. The plasmid was constructed by the procedures described by Buell et al., *Nuc. Acids Res.*, 13(6):1923 [1985]. The gene is under the control of the strong leftward promoter ($P_L$) of bacteriophage λ and contains a ribosomal binding site derived from the ner gene of bacteriophage mu. The host cell also carries a plasmid, pCI857, coding for a temperature-sensitive repressor protein so that gene expression can be induced by raising the temperature of the culture medium above about 42° C., thereby inactivating the repressor.

The DNA sequence of the synthetic SmC gene insert in pGB725, and the encoded amino acid sequence of rhSmC are given in FIG. 1. A partial restriction map of pGB725 is given in FIG. 2. *E. coli* HB101 [hsd, recA, ara, proA,lacY, galK, rpsL, xyl, mtl, supE] transformed with pGB725 and pCI857 has been deposited with the American Type Culture Collection, Rockville, Md., with accession No. ATCC 53551.

The rhSmC can be recovered from *E. coli* cells and purified prior to subjecting it to the method of this invention by any conventional methods of protein purification. In a preferred procedure, the fermentation broth containing the cells is centrifuged and the cells are recovered as a wet cell paste. The cells are then resuspended in a suitable buffer for cell breakage, such as lysozyme buffer (0.1M tris-HCl, 5 mM β-mercaptoethanol, 10 mM EDTA, 5 mM benzamidine-HCl, 0.2 mg/ml lysozyme, pH 7.5). The resuspended cells are then lysed mechanically, e.g., in a Manton-Gaulin homogenizer. The lysed cells are centrifuged and an inclusion pellet containing the rhSmC is recovered. The inclusion pellet is washed once in 0.1M tris-HCl pH 7.5, 5 mM β-mercaptoethanol, 10 mM EDTA. The rhSmC is then extracted and solubilized (denatured) in 6M guanidine hydrochloride. The guanidine solution is then diluted ten-fold in cold buffer, which causes solubilized rhSmC to refold to its soluble, native configuration. The solution is centrifuged and the precipitated pellet is discarded. The rhSmC is recovered by ammonium sulfate precipitation. After salt removal by dialysis against salt-free buffer, the rhSmC is purified by anion exchange chromatography on a DEAE-Sepharose CL6B column followed by gel filtration chromatography on a Sephadex G-50 column. The purified rhSmC obtained from the gel filtration column is suitable for resolution into two ionic forms by the method of the invention. It is to be understood, however, that the purification scheme is preliminary to the isolation procedure of the invention and that any of various other purification schemes can be employed in its stead.

In accordance with the method of the invention, an aqueous solution of purified SmC is applied to a strong cation-exchange column. Strong cation-exchange columns are generally those which have bound to the solid support a ligand that has a pKa value less than or equal to about 2. Preferred cation-exchange columns for use in the practice of the invention are those in which the functional group on the ligand is a sulfonic acid group. A particularly preferred cation-exchange column is known as SP-Sephadex C-25 and is commercially available from Pharmacia, Inc., Piscataway, N.J. SP-Sephadex C-25 contains sulfopropyl groups bound to a dextran support.

The SmC is loaded onto the cation-exchange column in a buffered solution at a pH at which the protein is stable, i.e., a pH from about 4.5 to about 6.5. The SmC, which becomes bound to the column, is then eluted from the column at an essentially constant pH by applying an aqueous salt gradient to the column. By "essentially constant" is meant that the pH should not be allowed to vary by more than about 0.2 during the elution. The elution pH is preferably the same as the pH of the SmC solution that is loaded onto the column, i.e., from about 4.5 to 6.5 and is most preferably about 5.5.

A preferred salt for use in the eluting buffer is ammonium acetate, since the ammonium acetate is easily volatilized for removal from the SmC. Other salts may be employed, however, including, but not limited to, sodium acetate, potassium acetate, ammonium formate, sodium formate and potassium formate. The concentration gradient can be obtained by continuous gradation of the elution buffer salt concentration or by a stepwise gradation. Preferably, the SmC is eluted from the column by applying a salt concentration gradient beginning at a concentration of about 10 mM and ending at about 200 mM. The eluant is collected in fractions as it leaves the column. SmC activity in the various elution fractions can be determined by any convenient method, such as by radioimmunoassay or radioreceptor assay.

The two ionic forms of SmC elute in different eluant fractions. When the column was eluted with ammonium acetate (pH 5.5), a first ionic form of SmC was recovered in the eluant fractions having ammonium acetate concentrations from about 50 mM to about 60 mM and a second ionic form of SmC was recovered in the eluant fractions having ammonium acetate concentrations from about 90 mM to about 110 mM. The former ionic form had a pI of 6.7-7.0 and the latter a pI of 8.3-8.6. Each of the ionic forms can be recovered from their respective elution buffer fractions by salt removal using conventional means such as dialysis. In the case of ammonium acetate, the elution buffer salt can easily be removed by volatilization. If desired, either of the two ionic forms can be lyophilized by conventional procedures for reconstitution at the time of use.

The pI 8.3-8.6 SmC, which is recovered free of other ionic forms by the method of the invention, corresponds to native-sequence SmC (predicted pI 8.6). It is uncertain whether the lower-pI form was produced from the native-sequence material in vivo or as an artifact of purification. The lower-pI material is believed to differ from the higher pI (native sequence) by a deamidation at amino acid position 26 which converts the asparagine residue normally present to an aspartic acid residue. The lower-pI material is distinguished from the possible deamidated form identified by Enberg and coworkers, supra, which contained a putative deamidation site at the glutamine of position 40. The amide group of the asparagine residue at position 26 is orders of magnitude more labile, and thus more prone to deamidation, than the corresponding groups of the glutamine residues at positions 15 and 40 due to the juxtaposition of the ε-amino group of the lysine residue at position 27.

Both ionic forms isolated by the method of the invention display biological activity in vitro in the placental radioreceptor and fibroblast growth assays. However, the particular ionic form which will be administered as a growth-promoting agent may depend on the particular application or mode of administration. It is believed that deamidation at Asn (26) occurs in vivo and that this event is related to the release of SmC from its associated carrier protein. SmC is transported in plasma in association with a carrier protein and must be released from the carrier protein at the site of its target cells.

Accordingly, if the SmC is to be administered by a mode of administration which requires transport through the blood system, it may be preferred to administer the native-sequence (higher pI) material essentially free of the deamidated form. If the SmC is to be administered directly to the site of the target tissues, then the lower pI, deamidated form, essentially free of native sequence material having asparagine at position 26 may be preferred.

The two ionic forms of SmC can be administered as growth-promoting agents, for example, in the treatment of hypopituitary dwarfism or to facilitate wound healing. In veterinary applications, the SmC can be administered to increase the rate of growth and feed utilization of cattle. The SmC can be administered alone or in conjunction with other growth-promoting substances such as human growth hormone, epidermal growth factor and the like. The SmC is administered in a growth-promoting amount in any suitable form for administration to an animal or human subject.

In one embodiment of the invention, there is provided a growth-promoting composition comprising a growth-promoting amount of somatomedin C having a pI of about 8.3 to 8.6, being essentially free of somatomedin C having a deamidated residue at amino acid position 26, and a pharmaceutically acceptable carrier vehicle. The pharmaceutical carrier can be, for example, a sterile aqueous buffer solution having a pH from about 4.5 to 6.5. The carrier material can also be a conventional cream or ointment base for topical application.

In another embodiment of the invention, there is provided a growth-promoting composition comprising a growth-promoting amount of somatomedin C having a pI of about 6.7 to 7.0 and having a deamidated residue at amino acid position 26, being essentially free of native-sequence somatomedin C, and a pharmaceutically acceptable carrier material. The pharmaceutical carrier can be, for example, a sterile aqueous buffer solution having a pH from about 4.5 to 6.5. The carrier material can also be a conventional cream or ointment base for topical application.

The following example illustrates further the practice of the invention and is not intended to limit the scope in any way.

EXAMPLE I

E. coli HB101 (pGB725 and pCI857), ATCC 53551 were cultured in a 10-liter fermentation in a medium containing 4% glycerol, 2% casamino acids, 0.3% yeast extract and salts, pH 7.0, and oxygen to 30% saturation. Following inoculation, the cells were fermented for 24 hours at 28° C., during which time expression of the rhSmC gene was repressed by the repressor protein coded for on plasmid pCI857. The temperature was then raised to 42° C. to inactivate the repressor protein, thereby inducing expression of the rhSmC gene on pGB725. Induction was accompanied by a 10% addition of growth medium. After 3 hours of culturing at 42° C., the cells were harvested by centrifugation.

The wet cell paste (280 gm) was resuspended in lysozyme buffer (pH 7.5, 1200 ml). Cells were then lysed by passage through a Manton-Gaulin homogenizer and centrifuged at 6000 ×g. The pellet (30 gm) was washed in 0.1M tris, pH 7.5 and extracted into 300 ml of 6M guanidine-HCl (pH 7.5). After 60 minutes, the denatured protein was renatured by diluting the guanidine-HCl with the addition of 3500 ml of 0.1M tris-HCl pH 7.5, 10 mM $\beta$-mercaptoethanol, 50 gm/L $(NH_4)_2SO_4$ buffer (0° C.). The solution of renatured protein was centrifuged at 5000 ×g and the precipitate was discarded. The rhSmC was recovered by precipitation with 3.0 mM ammonium sulfate. The recovered protein (0.42 gm) was dialyzed 2× against 10 volumes of 0.1 tris-HCl, 5 mM $\beta$-mercaptoethanol, 6M urea pH 8.4. The protein was then loaded onto a 25 cm×100 cm DEAE-Sepharose CL6B anion-exchange column. This was followed by gel filtration chromatography on a Sephadex G-50 5×100 cm. The columns were eluted with 0.85M ammonium acetate, pH 5.5. Peak fractions were collected and dialyzed 2 ×vs. 2 water, then lyophilized.

The rhSmC was then chromatographed on a protein pre-treated 0.7 cm×10 cm SP-Sephadex C-25 column.

The rhSmC (1.08 mg) was dissolved in 10 mM ammonium acetate, pH 5.56 to 1 mg/ml and loaded onto the column. The rhSmC was then eluted from the column by applying a linear gradient of ammonium acetate from 10 mM to 200 mM at a rate of 0.34 mM/min. The pH remained constant throughout the elution procedure. Eleven-minute fractions (3.96 ml) were collected. The elution was continued isocratically overnight at the final buffer concentrations, 200 mM ammonium acetate, pH 5.5. FIG. 3 is a chromatograph, showing four visible peaks. The following fractions were pooled and concentrated for analysis.

| Pool No. | Fractions in Pool | Description |
|---|---|---|
| 1 | 2 | Peak 1 |
| 2 | 3-4 | Peak 2 |
| 3 | 8-17 | Peak 3 |
| 4 | 18-21 | Leading shoulder Peak 4 |
| 5 | 22-25 | Peak 4 |
| 6 | 26-34 | Trailing shoulder Peak 4 |
| 7 | 35-70 | Peak 5 |

SDS-polyacrylamide gel electrophoresis of pooled fractions indicated that all the fractions except No. 1 and 7 contained a predominant band corresponding to rhSmC. Aliquots from each pooled fraction were hydrolyzed for 24 hours for amino acid analysis. Comparison of the results with the theoretical molar ratios of amino acids in SmC indicated that the major pooled fractions No. 4, 5 and 6 were very consistent with expected values and pooled fraction No. 3 was consistent with SmC, although there was a slight variation of ±1-3 residues. The data for pooled fractions No. 1, 2 and 7 showed that these fractions contained major peptides which were not rhSmC.

Pooled fractions No. 3 through 7 were assayed for SmC activity by radioreceptor assay on the placental SmC receptor assay (Marshall, R. N. et al., 1974 Characterization of the Insulin and Somatomedin-C Receptors in Human Placental Cell Membranes, J. Clin. Endoc. and Mitab., 39:283-292). Results showed that pooled fractions No. 3 through 6 all bound to the placental receptor with high affinity The pI values for SmC species in all eluted fractions were confirmed by IEF analysis of the pooled peak fractions. Pool No. 3 constitutes SmC, pI 6.7-7.0 and pools Nos. 4-6, SmC, pI 8.3-8.6.

What is claimed is:

1. A method of separating and isolating two ionic forms of somatomedin C which comprises applying an aqueous solution of purified or partially purified somatomedin C at a pH from about 4.5 to about 6.5 to a cation-exchange column having bound to a solid support a ligand which has an ionizing group with a pka $\leq 2$; eluting the somatomedin C from the column at an essentially constant pH by applying an aqueous salt gradient to the column; and recovering the two ionic forms of somatomedin C in different eluant fractions.

2. A method as claimed in claim 1, wherein the ionizing group of the ligand is a sulfonic acid.

3. A method as claimed in claim 1, wherein the cation-exchange column is a SP-Sephadex C-25 column.

4. A method as claimed in claim 1, wherein the aqueous solution of purified somatomedin C is applied to the cation-exchange column at a pH of about 5.5.

5. A method as claimed in claim 1, wherein the somatomedin C is eluted from the column by applying a concentration gradient of aqueous ammonium acetate to the column.

6. A method as claimed in claim 5, wherein the concentration gradient is applied continuously to the column.

7. A method as claimed in claim 5, wherein the concentration gradient is applied in a stepwise manner to the column.

8. A method as claimed in claim 5, wherein the concentration gradient of ammonium acetate is from 10 mM to 200 mM.

9. A method as claimed in claim 5, wherein a first ionic form of somatomedin C is recovered in the eluant fractions having ammonium acetate concentrations from about 50 mM to aobut 60 mM and a second ionic form of somatomedin C is recovered in the eluant fractions having ammonium acetate concentrations from about 90 mM to about 110 mM.

10. A composition comprising somatomedin C having a pI of about 6.7-7.0 and a deamidated residue at amino acid position 26, the composition being essentially free of somatomedin C having an asparagine residue at position 26, and a pharmaceutically acceptable carrier.

11. The composition of claim 10 which comprises an aqueous solution of from about 50 mM to about 60 mM of ammonium acetate and somatomedin C having a pI of about 6.7-7.0 and a deamidated residue at position 26, the solution being essentially free of somatomedin C having an asparagine residue at amino acid position 26.

12. An ionic for of somatomedin C having a pI of about 6.7-7.0 and a deamidated residue at amino acid position 26.

13. An ionic form of somatomedin C produced by the process of claim 1 having a pI of about 6.7-7.0 and a deamidated residue at position 26.

* * * * *

UNITED STATES PATENT AND TRADEMARK OFFICE
CERTIFICATE OF CORRECTION

PATENT NO. : 4,769,361
DATED : September 6, 1988
INVENTOR(S) : B. D. Burleigh and D. S. Murphy It is certified that error appears in the above-identified patent and that said Letters Patent is hereby corrected as shown below:

Column 6, line 13, "2 water" should read -- 2 1 water --

In the Abstract, line 1, "6.4-7.0" should read -- 6.7-7.0 --

Signed and Sealed this

Nineteenth Day of September, 1989

Attest:

DONALD J. QUIGG

Attesting Officer

Commissioner of Patents and Trademarks